United States Patent [19]

Stoltefuss et al.

[11] Patent Number: 5,504,209

[45] Date of Patent: Apr. 2, 1996

[54] 2-AMINO-5-CYANO-4-QUINOLYDIHYDROPYRIDINE ESTERS, PROCESSES FOR THEIR PREPARATION AND THEIR USE IN MEDICAMENTS

[75] Inventors: Jürgen Stoltefuss, Haan; Siegfried Goldmann, Wuppertal; Alexander Straub, Wuppertal; Martin Bechem, Wuppertal; Rainer Gross, Wuppertal; Siegbert Hebisch, Bottrop; Joachim Hütter; Howard-Paul Rounding, both of Wuppertal, all of Germany

[73] Assignee: Bayer Aktiengesellschaft, Leverkusen, Germany

[21] Appl. No.: 230,281

[22] Filed: Apr. 20, 1994

[30] Foreign Application Priority Data

Apr. 27, 1993 [DE] Germany ............ 43 13 695.8

[51] Int. Cl.6 ............ C07D 401/04; C07D 401/14; A61K 31/47
[52] U.S. Cl. ............ 546/167; 514/314
[58] Field of Search ............ 546/167; 514/314

[56] References Cited

U.S. PATENT DOCUMENTS

| | | | |
|---|---|---|---|
| 3,862,162 | 1/1975 | Meyer et al. | 260/295.5 |
| 3,989,708 | 11/1976 | Meyer et al. | 516/295.5 B |
| 4,532,248 | 7/1985 | Franckowiak et al. | 514/302 |
| 5,225,558 | 7/1993 | Stoltefuss et al. | 546/167 |

FOREIGN PATENT DOCUMENTS

| | | |
|---|---|---|
| 0071819 | 2/1983 | European Pat. Off. . |
| 0073997 | 3/1983 | European Pat. Off. . |
| 0515940 | 12/1992 | European Pat. Off. . |

*Primary Examiner*—David B. Springer
*Attorney, Agent, or Firm*—Sprung Horn Kramer & Woods

[57] ABSTRACT

The present invention relates to new 2-amino-5-cyano-4-quinolyl-1, 4-dihydropyridine esters of the general formula (I)

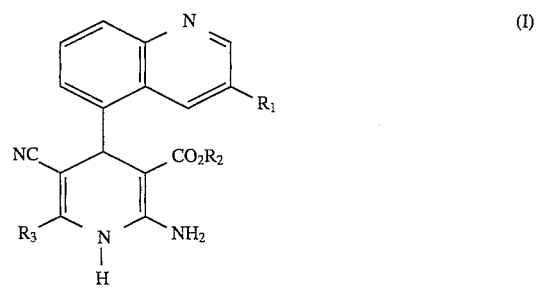

in which $R_1$ to $R_3$ have the meaning given in the description, to processes for their preparation and to their use in medicaments, especially in agents for the treatment of cardiac circulatory disorders.

5 Claims, No Drawings

2-AMINO-5-CYANO-4-QUINOLYDIHYDROPYRIDINE ESTERS, PROCESSES FOR THEIR PREPARATION AND THEIR USE IN MEDICAMENTS

The present invention relates to new 2-amino-5-cyano-4-quinolyl-1,4-dihydropyridine esters, to processes for their preparation and to their use in medicaments, especially in agents for the treatment of cardiac circulatory disorders.

It is already known that some 2- and 6-amino-3,4-dihydropyridines, in addition to possessing an antiarrhyttunic action, are also active in inhibiting lipid absorption. 2-Amino-1,4-dihydropyridines having a vasodilatory and antihypertensive action have also already been described.

Some of the compounds of the formula (I) according to the invention are covered by the general, broad description in EP 71 819, although without being mentioned specifically therein. Additionally, EP A 515 940 describes 2-amino-5-cyano-4-quinolyl-dihydropyridines which have a positively inotropic action.

The present invention relates to new 2-amino -5-cyano-4-quinolyldihydropyridine esters of the general formula (I)

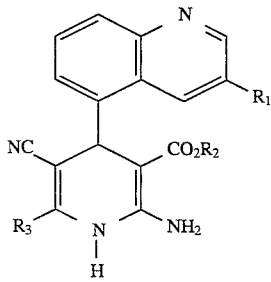

in which $R^1$ represents aryl having from 6 to 10 carbon atoms which is optionally substituted up to 3 times by identical or different substituents comprising halogen, nitro, cyano, hydroxyl, trifluoromethyl, trifluoromethoxy or trifluoromethylthio or by straight-chain or branched alkyl having up to 8 carbon atoms, which may in turn be substituted by aryl having from 6 to 10 carbon atoms, or is substituted by straight-chain or branched alkoxy or alkoxycarbonyl having in each case up to 8 carbon atoms, carboxyl, amino or a group of the formula $-NR^4R^5$, in which $R^4$ and $R^5$ are identical or different and denote hydrogen, straight-chain or branched alkyl having up to 8 carbon atoms, phenyl or benzyl, or represents pyridyl or thienyl, which are optionally substituted by halogen, $R^2$ represents a straight-chain, branched, cyclic, saturated or unsaturated hydrocarbon radical having up to 12 carbon atoms, which is in each case substituted once or twice by identical or different substituents comprising $-CO-NR^7R^8$, $-NR^9-CO-R^{10}$, $-NR^{11}-SO_2-R^{12}$, $-SO_2-NR^{13}R^{14}$, $O-NO_2$, $-O-(CH_2)_b-R^{15}$, $-S(O)_c-(CH_2)_d-R^{16}$, $-NR^{17}-COOR^{18}$ or $-NR^{19}R^{20}$ in which $R^7$, $R^8$, $R^9$, $R^{10}$, $R^{11}$, $R^{12}$, $R^{13}$, $R^{14}$, $R^{17}$ and $R^{18}$ are identical or different and have the meaning of $R^6$ given and are identical to or different from the latter, b denotes a number 1, 2, 3, 4 or 5, d denotes a number 0, 1, 2, 3, 4 or 5, c has the meaning of a given below and is identical to or different from the latter, and $R^{15}$ and $R^{16}$ are identical or different and denote aryl having from 6 to 10 carbon atoms which is optionally substituted up to twice by identical or different substituents comprising halogen, nitro, amino, hydroxyl or carboxyl, or by straight-chain or branched alkyl, alkoxy or alkoxycarbonyl having in each case up to 4 carbon atoms, $R^{19}$ and $R^{20}$ are identical or different and denote straight-chain or branched alkyl having from 2 to 8 carbon atoms which is substituted by halogen, hydroxyl or phenyl which may in turn be substituted by halogen, nitro or hydroxyl or by straight-chain or branched alkyl or alkoxy having in each case up to 4 carbon atoms, or cycloalkyl having from 3 to 8 carbon atoms, or straight-chain or branched alkenyl having from 3 to 8 carbon atoms, or phenyl which is substituted by halogen or nitro or straight-chain or branched alkyl or alkoxy having up to 4 carbon atoms, or $R^{19}$ and $R^{20}$, together with the nitrogen atom, form a 4- to 7-membered heterocycle which is optionally interrupted by an oxygen or sulphur atom or by a radical of the formula $-NR^{21}$, in which $R^{21}$ denotes hydrogen or straight-chain or branched alkyl having up to 8 carbon atoms which is optionally substituted by phenyl which may in turn be substituted by halogen, or phenyl which is optionally substituted by halogen, or is substituted by a 3- to 7-membered saturated or unsaturated heterocycle or heterocyclyloxy ring having up to 3 heteroatoms from the series S, N or O which may in turn be substituted up to twice by identical or different substituents comprising halogen or hydroxyl or by aryl or arylsulphonyl having from 6 to 10 carbon atoms, the rings in turn being able to be substituted up to twice by identical or different substituents comprising halogen, nitro, amino, hydroxyl or carboxyl or by straight-chain or branched alkyl, alkoxy or alkoxycarbonyl having in each case up to 6 carbon atoms, or the heterocycle is optionally substituted up to twice by identical or different substituents comprising straight-chain or branched alkyl or alkenyl having in each case up to 8 carbon atoms, which may in turn be substituted up to twice by identical or different substituents $-NR^{22}R^{23}$, in which $R^{22}$ and $R^{23}$ are identical or different and denote hydrogen or a straight-chain, branched, saturated, unsaturated or cyclic hydrocarbon radical having up to 8 carbon atoms which is optionally substituted up to twice by identical or different substituents comprising hydroxyl, halogen or cycloalkyl having from 3 to 6 carbon atoms or by aryl or aryloxy having from 6 to 10 carbon atoms, which may in turn be substituted up to twice by identical or different substituents comprising halogen, nitro, amino, hydroxyl or carboxyl or by straight-chain or branched alkyl, alkoxy or alkoxycarbonyl having in each case up to 6 carbon atoms, or aryl having from 6 to 10 carbon atoms which is optionally substituted up to twice by identical or different substituents comprising halogen, nitro, amino, hydroxyl or carboxyl or by straight-chain or branched alkyl, alkoxy or alkoxycarbonyl having in each case up to 6 carbon atoms, or R²² and R²³, together with the nitrogen atom, form a 5- to 7-membered saturated or unsaturated heterocycle having up to 3 heteroatoms from the series S, N or O, or alkyl or alkenyl may in turn be substituted by phenyl or phenoxy, which are optionally substituted up to twice by identical or different substituents comprising halogen, nitro, amino, hydroxyl or carboxyl or by straight-chain or branched alkyl, alkoxy or alkoxycarbonyl having in each case up to 6 carbon atoms, which may optionally be interrupted by an oxygen atom or by arylidene having from 6 to 10 carbon atoms which is optionally substituted by halogen, nitro, amino, hydroxyl or carboxyl or by straight-chain or branched alkyl, alkoxy or alkoxycarbonyl having in each case up to 6 carbon atoms or which is optionally substituted by a group of the formula —S(O)$_a$ or —NR⁶, in which a denotes a number 0, 1 or 2 and R⁶ denotes hydrogen, aryl having from 6 to 10 carbon atoms or straight-chain or branched alkyl having up to 6 carbon atoms or cycloalkyl having from 3 to 8 carbon atoms, with alkyl and cycloalkyl being optionally substituted by aryl having from 6 to 10 carbon atoms, and with the hydrocarbon radical being optionally substituted, in addition, by phenyl which may in turn be substituted by halogen, and R³ represents hydrogen or represents straight-chain or branched alkyl having up to 8 carbon atoms, and salts thereof.

Possible physiologically acceptable salts may be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid or benzoic acid, or methanesulphonic acid, ethanesulphonic acid, phenylsulphonic acid, toluenesulphonic acid or naphthalenedisulphonic acid.

The compounds according to the invention exist in stereoisomeric forms which are either mirror images of one another (enantiomers) or otherwise (diastereomers). The invention relates not only to the optical isomers but also to the racemic forms and to the mixtures of diastereomers. Both the racemic forms and the diastereomers can be separated in a known manner into the stereoisomerically uniform components.

Preferred compounds of the general formula (I) are those in which

R¹ represents phenyl which is optionally substituted up to twice by identical or different substituents comprising halogen, nitro, cyano, hydroxyl or trifluoromethyl or by straight-chain or branched alkyl or alkoxy having in each case up to 4 carbon atoms or by a group of the formula —NR⁴R⁵, in which R⁴ and R⁵ are identical or different and denote hydrogen, straight-chain or branched alkyl having up to 6 carbon atoms, phenyl or benzyl, or represents pyridyl or thienyl which are optionally substituted by fluorine, chlorine or bromine, R² represents a straight-chain, branched, cyclic, saturated or unsaturated hydrocarbon radical having up to 10 carbon atoms, which is in each case substituted once or twice by identical or different substituents comprising —CO—NR⁷R⁸, —NR⁹—CO—R¹⁰, —NR¹¹—SO₂—R¹², —SO₂—NR¹³R¹⁴, O—NO₂, —O—(CH₂)$_b$—R¹⁵, —S(O)$_c$—(CH₂)$_d$—R¹⁶, —NR¹⁷—COOR¹⁸ or —NR¹⁹R²⁰ in which

R⁷, R⁸, R⁹, R¹⁰, R¹¹, R¹², R¹³, R¹⁴, R¹⁷ and R¹⁸ are identical or different and have the meaning of R⁶ given below, and are identical to or different from the latter, b denotes a number 1, 2, 3 or 4, d denotes a number 0, 1, 2, 3 or 4, c has the meaning of a given below and is identical to or different from the latter, R¹⁵ and R¹⁶ are identical or different and denote phenyl which is optionally substituted up to twice by identical or different substituents comprising fluorine, chlorine, nitro or carboxyl or by straight-chain or branched alkyl, alkoxy or alkoxycarbonyl having in each case up to 4 carbon atoms, R¹⁹ and R²⁰ are identical or different and denote straight-chain or branched alkyl having from 2 to 8 carbon atoms which is substituted by fluorine, chlorine, bromine or phenyl which may in turn be substituted by fluorine, chlorine, bromine, methyl, ethyl, methoxy or ethoxy, or denote cyclopropyl, cyclopentyl or cyclohexyl, or denote phenyl which is substituted by fluorine, chlorine, bromine, nitro, methyl, ethyl, methoxy or ethoxy, or R¹⁹ and R²⁰, together with the nitrogen atom, form a 5- to 7-membered heterocycle which is optionally interrupted by an oxygen or sulphur atom or by a radical of the formula —NR²¹, in which R²¹ denotes hydrogen or straight-chain or branched alkyl having up to 10 carbon atoms which is optionally substituted by phenyl which may in turn be substituted by fluorine, chlorine or bromine, or denotes phenyl which is optionally substituted by fluorine, chlorine or bromine, or is substituted by pyridyl, tetrahydropyranyl, pyrazolyl, furyl, chromanyl, piperazinyl, piperidinyl, isoquinolidinyl or by a radical of the formula

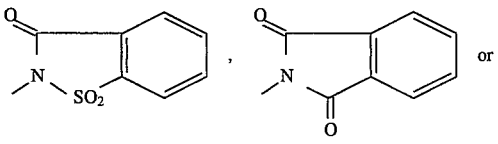

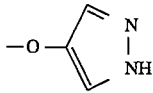

which may in turn be substituted by fluorine, benzyl, phenyl or phenylsulphonyl, and where the hydrocarbon radical (R²) is optionally interrupted, in addition, by oxygen, by phenylidene or by —S(O)$_a$ or —NR⁶, in which a denotes a number 0, 1 or 2 and R⁶ denotes hydrogen, phenyl or straight-chain or branched alkyl having up to 5 carbon atoms, cyclopropyl, cyclopentyl or cyclohexyl, which are optionally substituted by phenyl and where the hydrocarbon radical is optionally substituted by phenyl which may in turn be substituted by fluorine, chlorine or bromine, $R^3$ represents hydrogen or straight-chain or branched alkyl having up to 4 carbon atoms, and salts thereof.

Particularly preferred compounds of the general formula (I) are those
in which $R^1$ represents phenyl which is optionally substituted up to twice by identical or different substituents comprising fluorine, chlorine, nitro, cyano, hydroxyl, trifluoromethyl, methyl, ethyl, methoxy or ethoxy or by a group of the formula —$NR^4R^5$,
in which $R^4$ and $R^5$ are identical or different and denote hydrogen, straight-chain or branched alkyl having up to 4 carbon atoms, phenyl or benzyl, or represents pyridyl or thienyl, $R^2$ represents a straight-chain, branched, cyclic, saturated or unsaturated hydrocarbon radical having up to 6 carbon atoms which is in each case substituted by a group —$CO—NR^7R^8$, —$NR^9—CO—R^{10}$, —$NR^{11}—SO_2—R^{12}$, $SO_2—NR^{13}R^{14}$, $O—NO_2$, —$O—(CH_2)_b—R^{15}$, —$S(O)_c—(CH_2)_d—R^{16}$, —$NR^{17}—COOR^{18}$ or —$NR^{19}R^{20}$, in which $R^7$, $R^8$, $R^9$, $R^{10}$, $R^{11}$, $R^{12}$, $R^{13}$, $R^{14}$, $R^{17}$ and $R^{18}$ are identical or different and have the meaning of $R^6$ given below, and are identical to or different from the latter, b denotes a number 1, 2, 3 or 4, d denotes a number 0, 1, 2, 3 or 4, c has the meaning of a given below and is identical to or different from the latter, $R^{15}$ and $R^{16}$ are identical or different and denote phenyl which is optionally substituted by fluorine, chlorine or nitro or by straight-chain or branched alkyl or alkoxy having in each case up to 3 carbon atoms, $R^{19}$ and $R^{20}$ are identical or different and denote straight-chain or branched alkyl having from 2 to 8 carbon atoms which is substituted by fluorine, chlorine, bromine or phenyl which may in turn be substituted by methyl, ethyl, methoxy or ethoxy, or denote cyclopropyl, cyclopentyl or cyclohexyl, or denote phenyl which is substituted by fluorine, chlorine, bromine, nitro, methyl, ethyl, methoxy or ethoxy, or $R^{19}$ and $R^{20}$, together with the nitrogen atom, form a 5- to 6-membered heterocycle which is optionally interrupted by an oxygen or sulphur atom or by a radical of the formula —$NR^{21}$,
in which $R^{21}$ denotes hydrogen or straight-chain or branched alkyl having up to 10 carbon atoms which is optionally substituted by phenyl which may in turn be substituted by fluorine, chlorine or bromine, or denotes phenyl which is optionally substituted by fluorine, chlorine or bromine, or the hydrocarbon radical is substituted by pyridyl, tetrahydropyranyl, furyl, chromanyl, piperazinyl or piperidinyl, or is substituted by a radical of the formula

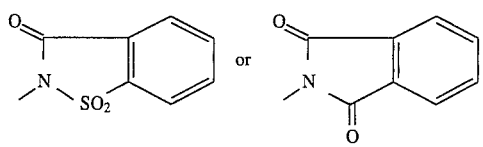

which may in turn be substituted by benzyl, and where the hydrocarbon radical ($R^2$) is optionally interrupted, in addition, by oxygen, phenylidene or by a group of the formula —$S(O)_a$ or —$NR^6$,
in which a denotes a number 0, 1 or 2
and $R^6$ denotes hydrogen, phenyl, benzyl or straight-chain or branched alkyl having up to 4 carbon atoms or cyclopropyl, cyclopentyl or cyclohexyl, and where the hydrocarbon radical is optionally substituted by phenyl which may in turn be substituted by fluorine, chlorine or bromine, and $R^3$ represents hydrogen or straight-chain or branched alkyl having up to 3 carbon atoms,
and salts thereof.

Very particularly preferred compounds of the general formula (I) are those
in which $R^1$ represents phenyl which is optionally substituted up to twice by identical or different substituents comprising fluorine, chlorine, cyano, hydroxyl, nitro, trifluoromethyl, methyl, methoxy or —$NR^4R^5$,
in which $R^4$ and $R^5$ are identical or different and denote hydrogen or straight-chain or branched alkyl having up to 4 carbon atoms, phenyl or benzyl, or represents pyridyl or thienyl, $R^2$ represents a straight-chain, branched, cyclic, saturated or unsaturated hydrocarbon radical having up to 6 carbon atoms, which is in each case substituted by —$CO—NR^7R^8$, —$NR^9—CO—R^{10}$, —$NR^{11}—SO_2—R^{12}$, —$SO_2—NR^{13}R^{14}$, $O—NO_2$, —$O—(CH_2)_b—R^{15}$, —$S(O)_c—(CH_2)_d—R^{16}$, —$NR^{17}—COOR^{18}$ or —$NR^{19}R^{20}$
in which $R^7$, $R^8$, $R^9$, $R^{10}$, $R^{11}$, $R^{12}$, $R^{13}$, $R^{14}$, $R^{17}$ and $R^{18}$ identical or different and have the meaning of $R^6$ given below, and are identical to or different from the latter, b denotes a number 1, 2, 3 or 4, d denotes a number 0, 1, 2, 3 or 4, c denotes a number 0 or 2, $R^{15}$ and $R^{16}$ denote phenyl, $R^{19}$ and $R^{20}$ are identical or different and denote straight-chain or branched alkyl having from 2 to 6 carbon atoms which is substituted by fluorine, chlorine or phenyl which may in turn be substituted by methyl or methoxy, or denote cyclopropyl, cyclopentyl or cyclohexyl, or denote phenyl which is substituted by fluorine, chlorine, methyl or methoxy, or $R^{19}$ and $R^{20}$, together with the nitrogen atom, form a 5- to 6-membered heterocycle which is optionally interrupted by an oxygen or sulphur atom or by a radical of the formula —$NR^{21}$,
in which $R^{21}$ denotes hydrogen or straight-chain or branched alkyl having up to 4 carbon atoms which is optionally substituted by phenyl, or is substituted by pyridyl or piperidyl, or by a radical of the formula

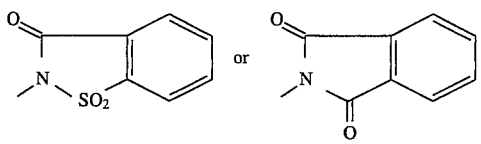

which may in turn be substituted by benzyl, or is interrupted by oxygen or by a group of the formula —NR⁶, in which R⁶ denotes hydrogen, phenyl, benzyl or straight-chain or branched alkyl having up to 4 carbon atoms, cyclopropyl, cyclopentyl or cyclohexyl, and where the hydrocarbon radical is optionally substituted by phenyl, and $R^3$ represents hydrogen or alkyl having up to 2 carbon atoms, and salts thereof.

The preparation of the compounds of the general formula (I) according to the invention is characterized in that [A] either aldehydes of the general formula (II)

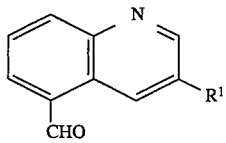

in which $R^1$ has the meaning given above, are reacted directly with compounds of the general formula (III)

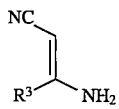

in which $R^3$ has the meaning given above, and compounds of the tautomeric formulae (IV) and (IVa)

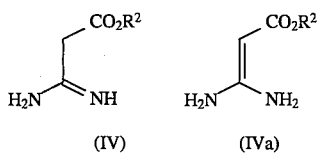

in which $R^2$ has the meaning given above, in inert solvents at temperatures of between 10° C. and 150° C., or

[B] ylidene compounds of the general formula (V)

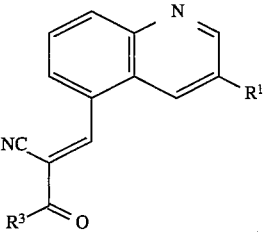

in which $R^1$ and $R^3$ have the meaning given above are reacted with compounds of the general formula (VI) or (VIa)

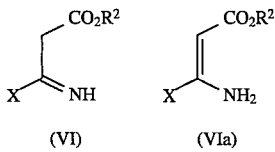

in which $R^2$ has the meaning given above and

X represents the amino group or $C_1$–$C_4$-alkoxy, optionally in the presence of inert organic solvents at temperatures of from 10° C. to 150° C.; if X represents $C_1$–$C_4$-alkoxy, ammonium salts such as ammonium acetate are added.

In the case of the pure enantiomers, either the mixture which is formed of diastereomers of the respective compounds of the general formula (I) in which $R^2$ represents a defined chiral radical is initially separated, then converted into the corresponding carboxylic acids ($R^2$=H) and, in a last step, esterified, or the respective diastereomers are transesterified directly using the corresponding alcohols, in particular in the form of the alcoholates.

The processes according to the invention can be illustrated by way of example by the following formula scheme:

[A]

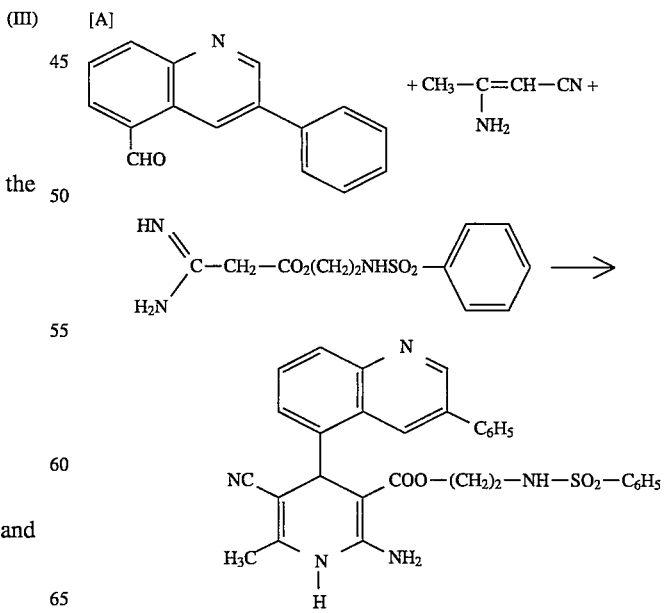

[B]

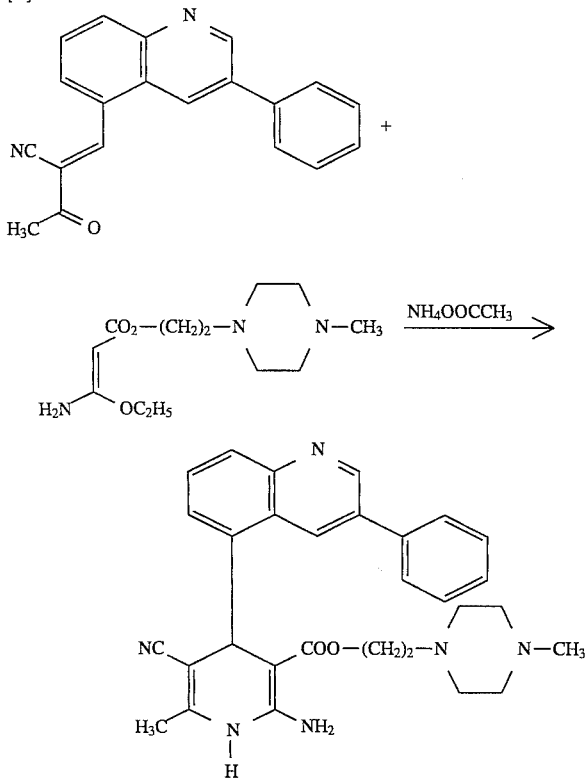

Suitable solvents in this context are all inert organic solvents which remain unchanged under the reaction conditions. Preferred solvents include alcohols such as methanol, ethanol, propanol or isopropanol, or ethers such as diethyl ether, dioxane, tetrahydrofuran, glycol dimethyl ether or diethylene glycol dimethyl ether, acetonitrile, or amides such as hexamethylphosphoric triamide or dimethylformamide, or acetic acid or halogenated hydrocarbons such as methylene chloride, carbon tetrachloride or hydrocarbons such as benzene or toluene. It is also possible to use mixtures of the solvents mentioned. Depending on the particular process variant [A] or [B], methanol, isopropanol, ethanol and n-propanol, acetonitrile or tetrahydrofuran are preferred.

The reaction temperatures can be varied over a wide range. It is in general carried out at between +10° C. and +150° C., preferably at between +20° C. and +100° C., and in particular at the boiling temperature of the respective solvent.

The reaction can be carried out at atmospheric pressure but also at increased or reduced pressure (e.g. from 0.5 to 3 bar). It is generally carried out at atmospheric pressure.

Suitable chiral ester radicals are all esters of enantiomerically pure alcohols such as, for example, 2-butanol, 1-phenylethanol, lactic acid, lactic acid esters, mandelic acid, mandelic acid esters, 2-aminoalcohols, sugar derivatives, hydroxyamino acid derivatives and many other enantiomerically pure alcohols.

The separation of the diastereomers is generally carried out either by fractional crystallization, by column chromatography or by Craig partition. Which is the best method must be decided from case to case; sometimes it is also expedient to use combinations of the individual methods. Particularly suitable separation is by crystallization or Craig partition, or by a combination of the two methods.

The compounds of the general formula (II) are in some cases known, or can be prepared by conventional methods by, for example, oxidizing the corresponding alkyl- or hydroxyalkyl-quinolines or reducing the corresponding carboxyquinolines.

As an alternative, 4-amino-3-hydroxyphthalide—which is obtained by conventional hydrogenation of 4-nitro-3-hydroxyphthalide, known from the literature, in the presence of a catalyst, preferably with palladium/barium sulphate—can also be reacted with compounds of the general formula $R^1$—$CH_2$—CHO, some of which are known [cf. e.g. Beilstein 7, 292] to give, via the corresponding carboxylic acids, compounds of the general formula (II).

The compounds of the general formulae (III), (IV) and (IVa) are known or can be prepared by methods known from the literature.

The ylidene compounds of the general formula (V) are known in some cases, or can be prepared by converting compounds of the general formula (VII)

 (VII)

in which $R^3$ has the meaning given above with alkali metal hydroxides or alkali metal alcoholates into the alkali metal salts of the compounds of the general formula (VIII)

$R^3$—CO—$CH_2$—CN   (VIII)

in which $R^3$ has the meaning given above, and reacting the salts, either in situ or after isolation, with aldehydes of the general formula (II) in one of the inert solvents listed above, preferably in alcohols, ethyl acetates, methylene chloride, acetonitrile, chloroform or ethers, with the addition of acid, preferably acetic acid, and optionally in the presence of a catalyst, for example piperidine acetate, at temperatures of between 0° C. and 150° C., preferably between 20° C. and 110° C.

The compounds of the general formulae (VI), (VIa), (VII) and (VIII) are known or can be prepared by conventional methods.

The compounds according to the invention exhibit an unforeseeable and valuable spectrum of pharmacological action. They influence myocardial contractility and smooth-muscle tone. They preferably have a positively inotropic action. They can therefore be employed in medicaments for influencing pathologically altered blood pressure, in coronary therapy, and for treating cardiac insufficiency. They can also be used for treating cardiac arrhythmias, for reducing blood sugar, for decongesting the mucosae and for influencing the salt and fluid balance.

The cardiac and vascular actions were demonstrated on the guinea-pig heart perfused in isolation. For this purpose, the hearts of guinea pigs weighing from 250 to 350 g are used. The animals are sacrificed by a blow to the head, the thorax is opened, and a metal cannula is inserted and attached in the exposed aorta. The heart and the lungs are excised from the thorax and connected via an aortic cannula, to the perfusion apparatus in the course of perfusion. The lungs are separated at the roots. The perfusion medium used is a Krebs-Henseleit solution (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$ and 0.013 mmol/l of $Na_2EDTA$) with a $CaCl_2$ content of 1.2 mmol/l. The energy-supplying substrate added is glucose at 10 mmol/l. Prior to the perfusion, the solution is filtered to remove all particles. The solution is gassed with carbogen (95% $O_2$, 5% $CO_2$) to maintain a pH of 7.4. The hearts are perfused at 32° C. at a constant flow rate (10 ml/min) using a peristaltic pump.

For measuring the cardiac function, a liquid-filled latex balloon which is connected via a liquid column with a pressure transducer is inserted through the left atrium into the left ventricle, and the isovolumetric contractions are recorded on a rapid recorder. The perfusion pressure is recorded using a pressure transducer which is connected to the perfusion system upstream of the heart. Under these conditions, a reduction in the perfusion pressure indicates a coronary dilatation, and an increase or decrease in the amplitude of contraction in the left ventricle indicates a fall or rise, respectively, in myocardial contractility. The compounds according to the invention, in suitable dilutions, are introduced into the perfusion system a short distance upstream of the isolated heart.

The new compounds can be converted by known methods into the conventional formulations such as coated and uncoated tablets, pills, granules, aerosols, syrups, emulsions, suspensions and solutions, using inert, non-toxic pharmaceutically appropriate excipients or solvents. In this context, the therapeutically active compound should in each case be present in a concentration of from approximately 0.5 to 90% by weight of the total mixture, i.e. in amounts sufficient to achieve the stated scope of dosage.

The formulations are prepared by, for example, extending the active compounds using solvents and/or excipients, with the optional use of emulsifiers and/or dispersants; where water is used as a diluent, organic solvents may optionally be used as auxiliary solvents.

Administration is made in a conventional manner, preferably orally or parenterally and, in particular, perlingually or intravenously.

It has in general proved advantageous, in the case of intravenous administration, to administer amounts of from approximately 0.001 to 1 mg/kg, preferably from approximately 0.01 to 0.5 mg/kg of body weight in order to achieve effective results; in the case of oral administration, the dosage is from approximately 0.01 to 20 mg/kg, preferably from 0.1 to 10 mg/kg of body weight.

Despite this, it may be necessary to depart from the stated amounts, specifically in dependence on the body weight or on the nature of the application route, on the individual response to the medicament, on the nature of its formulation and on the time at or over which administration is made. For instance, it may in some cases be sufficient to use less than the minimum amount stated above, while in other cases the upper limit mentioned has to be exceeded. In the case where greater quantities are administered, it may be advisable to distribute these in two or more individual doses over the day.

EXAMPLE 1

1S,2R-2-Benzyloxycarbonylamino-1-phenyl-propyl 2-amino-5-cyano-6-methyl-4-(3-phenyl-5-quinolinyl)-1,4-dihydropyridine-3-carboxylate

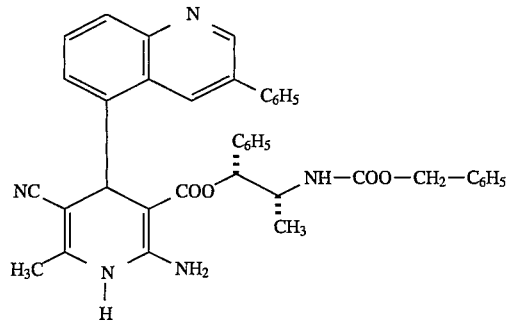

1.5 g (5 mmol) of 2-(3-phenyl-5-quinolylidene)-3-oxobutyronitrile in 10 ml of isopropanol are heated at reflux with 2 g (5 mmol) of 1S,2R-2-benzyloxycarbonylamino- 1-phenyl-propyl 3-ethoxy-3-imino-propionate and 770 mg of ammonium acetate for 18 hours. The mixture is cooled and concentrated. The residue is dissolved in ethyl acetate/water, the phases are separated, and the ethyl acetate phase is washed with water, dried and concentrated. The two diastereomers are separated on a silica gel column using dichloromethane/ethyl acetate mixtures. 514 mg of the diastereomer A with a melting point of from 159°–163° C. are obtained.

$R_f$ value =0.6, TLC aluminium sheet, Merck, dichloromethane/ethyl acetate =1:1

Diastereomer B: melting point: from 160° C.

$R_f$ value=0.48

The compounds listed in Table 1 are prepared in analogy to the procedure of Example 1:

TABLE 1

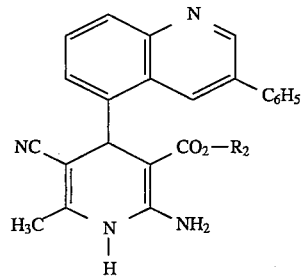

| Ex. No. | R² | m.p. °C. | Diastereomer | Enantiomer |
|---|---|---|---|---|
| 2 | —CH(C₆H₅)—CH(CH₃)—NH—CO₂—CH₂—C₆H₅ | >159° C. | A | |

TABLE 1-continued

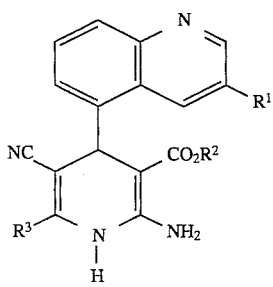

| Ex. No. | R² | m.p. °C. | Diastereomer | Enantiomer |
|---|---|---|---|---|
| 3 | —⟨cyclohexyl⟩—N—CH₂—C₆H₅ | 148–150 | | (−) |
| 4 | —(CH₂)₂—NH—COO—H₂C—⟨phenyl⟩ | 154–155 | | |

We claim:

1. A compound of the formula

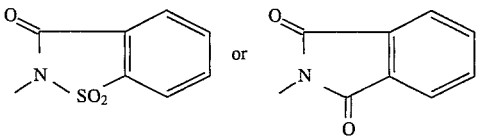

(I)

in which

R¹ represents phenyl which is optionally substituted up to twice by identical or different substituents comprising fluorine, chlorine, nitro, cyano, hydroxyl, trifluoromethyl, methyl, ethyl, methoxy or ethoxy or by a group of the formula —NR⁴R⁵, in which R⁴ and R⁵ are identical or different and denote hydrogen, straight-chain or branched alkyl having up to 4 carbon atoms, phenyl or benzyl, or represents pyridyl or thienyl, R² represents a straight-chain, branched, cyclic, saturated or unsaturated hydrocarbon radical having up to 6 carbon atoms which is in each case substituted by a group —CO—NR⁷R⁸, —NR⁹—CO—R¹⁰, —NR¹¹—SO₂—R¹², —SO₂—NR¹³R¹⁴, O—NO₂, —O—(CH₂)ᵦ—R¹⁵, —S(O)ᴄ—(CH₂)ᴅ—R¹⁶, —NR¹⁷—COOR¹⁸ or —NR¹⁹R²⁰, in which R⁷, R⁸, R⁹, R¹⁰, R¹¹, R¹², R¹³, R¹⁴, R¹⁷ and R¹⁸ are identical or different and have the meaning of R⁶ given below, and are identical to or different from the latter, b denotes a number 1, 2, 3 or 4, d denotes a number 0, 1, 2, 3 or 4, c has the meaning of a given below and is identical or different to the latter, R¹⁵ and R¹⁶ are identical or different and denote phenyl which is optionally substituted by fluorine, chlorine or nitro or by straight-chain or branched alkyl or alkoxy having in each case up to 3 carbon atoms, R¹⁹ and R²⁰ are identical or different and denote straight-chain or branched alkyl having from 2 to 8 carbon atoms which is substituted by fluorine, chlorine, bromine or phenyl which may in turn be substituted by methyl, ethyl, methoxy or ethoxy, or denote cyclopropyl, cyclopentyl or cyclohexyl, or denote phenyl which is substituted by fluorine, chlorine, bromine, nitro, methyl, ethyl, methoxy or ethoxy, or the hydrocarbon radical is substituted by pyridyl, tetrahydropyranyl, furyl, chromanyl, piperazinyl or piperidinyl, or is substituted by a radical of the formula

[structures: saccharin-like and phthalimide-like groups] or which may in turn be substituted by benzyl, and where the hydrocarbon radical (R²) is optionally interrupted, in addition, by oxygen, phenylidene or by a group of the formula —S(O)ₐ or —NR⁶, in which a denotes a number 0, 1 or 2 and R⁶ denotes hydrogen, phenyl, benzyl or straight-chain or branched alkyl having up to 4 carbon atoms or cyclopropyl, cyclopentyl or cyclohexyl, and where the hydrocarbon radical is optionally substituted by phenyl which may in turn be substituted by fluorine, chlorine or bromine, and R³ represents hydrogen or straight-chain or branched alkyl having up to 3 carbon atoms, or a pharmaceutically acceptable salt thereof.

2. The compound according to claim 1 in which

R¹ represents phenyl which is optionally substituted up to twice by identical or different substituents comprising fluorine, chlorine, cyano, hydroxyl, nitro, trifluoromethyl, methyl, methoxy or —NR$^4$R$^5$, in which R$^4$ and R$^5$ are identical or different and denote hydrogen or straight-chain or branched alkyl having up to 4 carbon atoms, phenyl or benzyl, or represents pyridyl or thienyl, represents a straight-chain, branched, cyclic, saturated or unsaturated hydrocarbon radical having up to 6 carbon atoms, which is in each case substituted by —CO—NR$^7$R$^8$, —NR$^9$—CO—R$^{10}$, —NR$^{11}$SO$_2$—R$^{12}$, —SO$_2$—NR$^{13}$R$^{14}$, O—NO$_2$, —O—(CH$_2$)$_b$—R$^{15}$, —S(O)$_c$—(CH$_2$)$_d$—R$^{16}$, —NR$^{17}$—COOR$^{18}$ or —NR$^{19}$R$^{20}$ in which R$^7$, R$^8$, R$^9$, R$^{10}$, R$^{11}$, R$^{12}$, R$^{13}$, R$^{14}$, R$^{17}$ and R$^{18}$ are identical or different and have the meaning of R$^6$ given below, and are identical to or different from the latter, b denotes a number 1, 2, 3 or 4, d denotes a number 0, 1, 2, 3 or 4, c denotes a number 0 or 2, R$^{15}$ and R$^{16}$ denote phenyl, and R$^{19}$ and R$^{20}$ are identical or different and denote straight-chain or branched alkyl having from 2 to 6 carbon atoms which is substituted by fluorine, chlorine or phenyl which may in turn be substituted by methyl or methoxy, or denote cyclopropyl, cyclopentyl or cyclohexyl, or denote phenyl which is substituted by fluorine, chlorine, methyl or methoxy, or is substituted by pyridyl or piperidyl, or by a radical of the formula

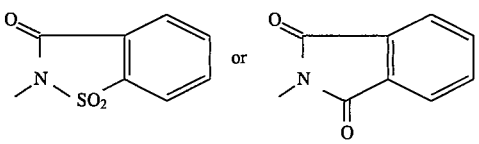

which may in turn be substituted by benzyl or is interrupted by oxygen or by a group of the formula —NR$^6$, in which R$^6$ denotes hydrogen, phenyl, benzyl or straight-chain or branched alkyl having up to 4 carbon atoms, cyclopropyl, cyclopentyl or cyclohexyl, and where the hydrocarbon radical is optionally substituted by phenyl, and R$^3$ represents hydrogen or alkyl having up to 2 carbon atoms, or a pharmaceutically acceptable salt thereof.

3. The compound according to claim 1 which is 2-Benzyloxy-carbonylamino-1-phenyl-propyl 2-amino-5-cyano-6-methyl-4-(3-phenyl-5-quinolinyl)-1,4-dihydropyridine-3-carboxylate.

4. A composition comprising a compound according to claim 1 and a pharmaceutically acceptable carrier.

5. A method of treating cardiac circulatory disorders which comprises administering a compound according to claim 1 to a host in need thereof.

* * * * *

UNITED STATES PATENT AND TRADEMARK OFFICE
CERTIFICATE OF CORRECTION

PATENT NO. : 5,504,209
DATED : April 2, 1996
INVENTOR(S) : Stoltefuss, et al.

It is certified that error appears in the above-indentified patent and that said Letters Patent is hereby corrected as shown below:

| | |
|---|---|
| Title Page & Col. 1 | [54] Line 2 delete " QUINOLYDIHYDROPY-RIDINE " and substitute -- QUINOLYL-DIHYDROPYRIDINE -- |
| Col. 15, line 7 | Delete " pyridy 1 " and substitute -- pyridyl -- |
| Col. 15, line 8 | Before " represents " insert -- $R^2$ -- |
| Col. 15, line 25 | Delete " and " (first occurrence) |

Signed and Sealed this

Twenty-fourth Day of September, 1996

Attest:

BRUCE LEHMAN

*Attesting Officer*     *Commissioner of Patents and Trademarks*